(12) United States Patent
Whitton

(10) Patent No.: US 7,153,313 B2
(45) Date of Patent: Dec. 26, 2006

(54) AURICULAR HEMATOMA CLAMP

(76) Inventor: Daniel F. Whitton, 18011 Bruno Rd., Justin, TX (US) 76247

(*) Notice: Subject to any disclaimer, the term of this patent is extended or adjusted under 35 U.S.C. 154(b) by 632 days.

(21) Appl. No.: 10/246,346

(22) Filed: Sep. 19, 2002

(65) Prior Publication Data

US 2004/0059353 A1    Mar. 25, 2004

(51) Int. Cl.
*A61B 17/08* (2006.01)
*A61F 13/00* (2006.01)

(52) U.S. Cl. ......................... 606/151; 602/53
(58) Field of Classification Search ................ 606/157, 606/158, 120, 116, 117, 151, 201, 204; 128/898; 24/501, 543; D30/144; 602/53
See application file for complete search history.

(56) References Cited

U.S. PATENT DOCUMENTS

| | | | | |
|---|---|---|---|---|
| 2,587,966 A | * | 3/1952 | Cleary ........................ | 606/151 |
| 3,456,262 A | * | 7/1969 | Coon .......................... | 24/501 |
| 3,698,043 A | * | 10/1972 | Batts .......................... | 24/543 |
| 3,874,042 A | | 4/1975 | Eddleman et al. ........... | 24/255 |
| 5,057,118 A | | 10/1991 | Picha ......................... | 606/158 |
| 5,423,853 A | * | 6/1995 | Lasvignes ................... | 606/204 |
| 5,515,872 A | * | 5/1996 | Martin et al. ............... | 128/898 |
| 5,827,212 A | * | 10/1998 | Gaskill ....................... | 602/53 |
| 6,517,557 B1 | * | 2/2003 | Sorribes ..................... | 606/151 |

* cited by examiner

*Primary Examiner*—Julian W. Woo
(74) *Attorney, Agent, or Firm*—Stephen S. Mosher

(57) ABSTRACT

An improved ear pressure device and process for the treatment of an auricular hematoma in a pendent ear of an animal. The device is comprised of two opposing rigid plates each containing at least one raised lineal or area encompassing rib located on an inward surface and used for applying pressure and controlling blood flow to and from the area treated. The process includes: aspirating pooled blood with a hypodermic needle: attaching the first plate to the ear with the raised rib toward the ear using athletic tape; aligning and attaching the opposing plate, rib facing inward, to the first plate and the ear; taping the entire device to the top of the animal's head with athletic tape over and under forming a loop around the head of the animal while allowing for normal breathing to occur. The device applies even pressure from both opposing plates and the raised ribs control the blood flow. The device and the process eliminates the need for surgery, sutures, and possible infection therefrom.

31 Claims, 3 Drawing Sheets

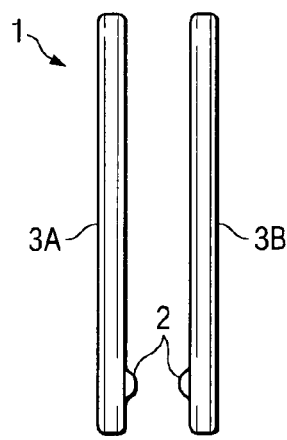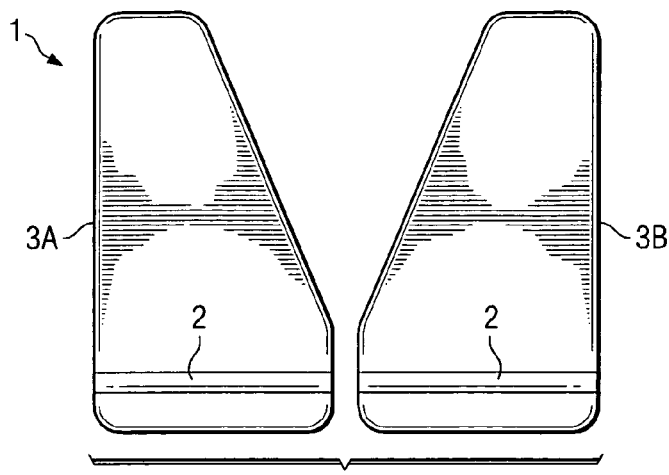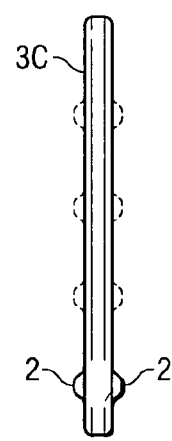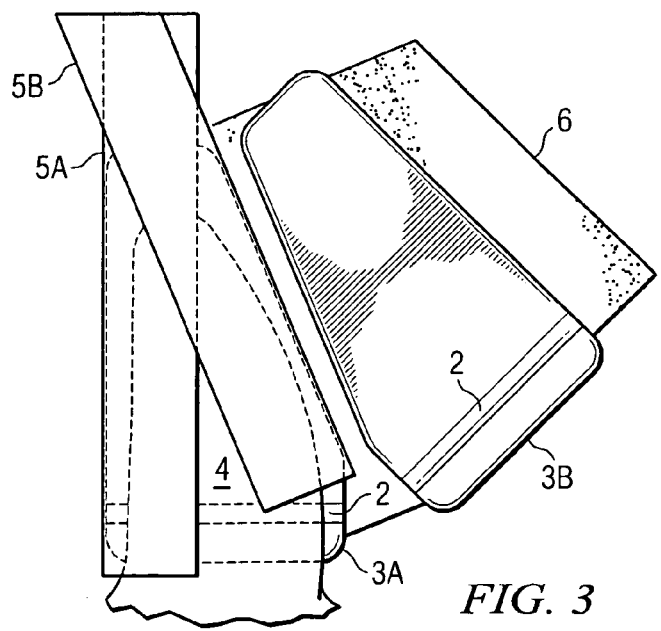

AURICULAR HEMATOMA CLAMP

BACKGROUND OF THE INVENTION

1. Field of the Invention

The present invention generally relates to a compression device in the field of veterinary medicine for use in the treatment of hematomas in the pendent ears of animals.

2. Background and Description of the Prior Art

Treatments such as surgery to repair the affected ear can cause infection, pain, and discomfort especially when associated with pressure devices for healing the hematoma including penetrations through the ear and conchal cartilage with sutures or wire securing devices. Surgery to the affected ear often leaves permanent scarring, wilting, shriveling to the ear. The opening of the inner, ear flap and suturing the broken blood vessel allows for possibility of infection. The use of quilting stitches to control the ear flap from expanding are uncomfortable for the animal. In addition, backing members used for the compression are made of heavy materials to retain their rigidity but add unneeded weight to the animals head and allow for discomfort to the animal. Furthermore, compression devices made of metal strips for conformity over the ear remain malleable and allow for expansion in the area of treatment.

As presented in U.S. Pat. No. 5,827,212, issued to Gaskill in October 1997, there are limitations associated with present ear pressure dressings to fill the need for a device and process providing such a dressing that is capable of applying a uniform pressure, with compression forces that are generally perpendicular to all of the relevant surfaces of the injured portion, which is minimally invasive, simple and expeditious to apply, and inexpensive.

There are problems with Gaskill's invention as it relates to auricular hematoma in animals. The use of a heavy material will cause discomfort due to the size of the plates required for performing the intended function. Attachment of Gaskill's invention requires penetration through the ear with a wire implement and securing the implement to retain pressure. The attachment through the ear and subsequent conchal cartilage can cause a tear in the pinna and may cause discomfort along with the possibility of infection.

As presented in U.S. Pat. No. 5,295,950, issued to Godley in October 1992, the ear pressure dressing is comprised of thin ductile material bendable to the desired form as to insure proper alignment with the opposite side of ear. There are limitations with this ear pressure dressing in respect to size and ability to create consistent pressure over a wide area such as the animal's pendent ear. The use of bendable material to perform the function of applying pressure at a point away from the helix can only produce a negative pressure difference at the point furthest from the helix thus exerting less pressure to the affected area.

As presented in U.S. Pat. No. 5,792,176, issued to Chang in August 1998, pressure devices are at present used for the purpose of providing controlled pressure to a selected point on the skin of a patient as per the field of the invention, acupressure.

As presented in U.S. Pat. No. 6,314,961, to Barnes in November 2001, the device for protecting newly cropped ears of animals is intended for post surgery, and to promote the earlier recovery from said surgery. The cause for surgery is elective and an ear portion is removed leaving much recovery to occur from underneath the protective cups.

Barnes improvement over the U.S. Pat. No. 4,221,189, issued to Olvera in September 1980, comprises the perforations for adjustment and the ventilated materials used for creating such cups. Both features would not work well with pendent ears.

SUMMARY OF THE INVENTION

The auricular hematoma clamp with a raised rib offers a healing solution for auricular hematoma in a pendent animal's ear without surgical treatments, lessens the chance of infection, and provides a less painful means to heal the hematoma. The auricular hematoma clamp is a simple device consisting of two opposing rigid plates, each said plate containing a raised rib rising from an inward surface, when positioned and attached to and over the ear and the opposing plate, form a clamp to prevent a hematoma from pooling in the pinna (auricle) while the raised ribs control the blood flow to and from the affected area. The auricular hematoma clamp is attached to the ear of the animal with athletic tape or a similar adhesive tape. The entire device is then attached to the head of the animal with a loop of tape over and under the head and neck of the animal. The plates are either flat or conform similar to the ear's shape. The raised ribs apply pressure to allow the controlled blood flow to and from the area of injured ear making healing recovery time sooner. The auricular hematoma clamp requires no need for surgery, eliminates the danger of rupture, and provides more comfort for the animal.

BRIEF DESCRIPTION OF THE DRAWINGS

FIG. 1 exhibits an auricular hematoma clamp comprised of two opposing plates, wherein each plate contains a raised rib rising from an inward surface;

FIG. 2A exhibits the ribs rising from the surface a small amount;

FIG. 2B exhibits an alternate embodiment of a plate of an auricular hematoma clamp of the present invention having a raised rib positioned in different locations along the surface of the plate;

FIG. 3 exhibits an auricular hematoma clamp comprised of two plates, each plate with a raised rib located on the inward surface, whereas one plate is shown properly positioned and secured with athletic tape to an affected ear, and the second plate is shown ready for attachment with athletic tape over ear and to the other plate;

DETAILED DESCRIPTION OF THE INVENTION

Figure 4:
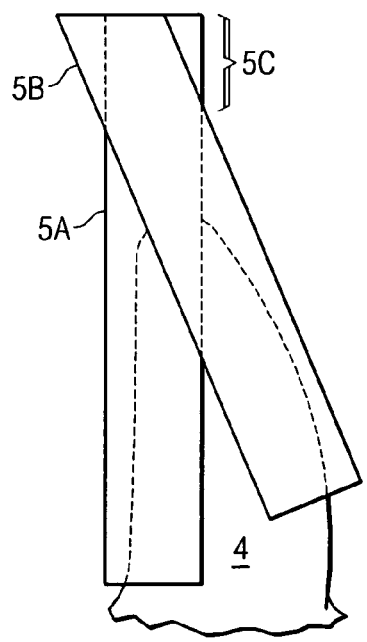
FIG. 4 exhibits that the athletic tape is first folded over the ear's edges forming tabs when the tape is extended beyond the ear.

The auricular hematoma clamp 1 illustrated in FIGS. 1 and 2A consists of two opposing plates 3A, 3B, each of said plates to be thin, rigid, lightweight, and contain at least one raised rib 2 rising above the inward surface facing toward the affected ear in direct opposition with other said plate. The rib 2 rises only a small amount above the surface of the plate 3A and 3B. The size and configuration of the plates 3A, 3B need to be slightly larger than and conform to ear of animal as to encompass and conceal the ear inside the clamp 1 (also called a device 1 herein). In specific instances, the plates of the auricular hematoma clamp may be smaller than the whole ear but remain large enough as to encompass the affected area while maintaining the raised ribs beyond the affected area. As shown in FIGS. 3 and 4, athletic tape 5A, 5B, and 6 is used to prepare the external ear (pinna) 4 for acceptance of the auricular hematoma clamp 1, by folding the tape 5A, 5B over the ear's (4) edges (helix) from the base end of the ear 4 at the animal's head to the outward end of the ear 4 leaving a segment beyond the outward end forming a tab 5C as shown in FIG. 4. Athletic tape 6, or a similar adhesive tape, is also used to secure the two opposing plates 3A, 3B together around the affected ear to form the clamp 1. With the device 1 secured to the ear and the tabs 5C exposed, the auricular hematoma clamp 1 is taped over the head of the animal to assist in prevention of blood pooling and to prevent flapping of the device 1 and the ear 4 by the animal. Proper care of the exposed under side of animal's ear 4 needs to be attended to while the auricular hematoma clamp 1 is in place to prevent foreign objects from entering the ear canal, and/or to prevent chaffing or abrasions from occurring to the softer tissues exposed.

Although the device 1 can remain in the pendent position and have healing occur, the chance of accidental removal by the animal may cause the treatment to be interrupted. The pendent position is not recommended for these reasons and the device would need to be properly reattached in the proper location for additional treatment.

Proper attachment of the auricular hematoma clamp 1 plates 3A, 3B to the ear 4 proceeds as follows, with further reference to FIGS. 3 and 4: aspirate the blood pool from the ear 4 with a hypodermic needle; prepare the affected ear 4 with tape 5A, 5B for attachment of the first opposing plate 3A; secure the first plate 3A to the ear 4 with tape 6 by folding the tape 6 over the first plate 3A and the ear 4 edges (helix), making sure the ear 4 is centered inside all edges of the plate 3A and that the raised rib 2 is towards the ear 4; carefully position the second plate 3B over the ear 4 and the first plate 3A, maintaining the proper position of the second plate 3B over the first plate 3A in parallel, which will correctly align the two opposing raised ribs 2 and allow the auricular hematoma clamp 1 to perform properly, tape the auricular hematoma clamp 1, with the ear 4 inside and the tab 5C exposed, to the top of the animal's head with a loop of tape (not shown) over and under animals head (not shown), making sure the loop of tape does not prohibit the animal from normal breathing; and, the animal must wear the auricular hematoma clamp 1 for several consecutive days for healing to occur.

The auricular hematoma clamp 1 can be worn with the ear in the pendent position, but the chance of the animal shaking the device 1 free, or dislodging the device 1 from the ear 4 is greater. Take care of the exposed under side of ear 4 to prevent chaffing and or debris accumulation. After five or more consecutive days, remove the auricular hematoma clamp 1 and let ear 4 rest for at least two days before attaching the auricular hematoma clamp 1 for an additional treatment. More than one treatment may be required to fully heal the hematoma.

The auricular hematoma clamp 1 fills the needs described, and with the use of the raised rib 2, sufficiently makes improvements to the treatments here associated.

The rigid material used for the auricular hematoma clamp 1 allows for even pressure to be applied across the surfaces of both plates 3A, 3B and insures consistency with respect to the plates 3A, 3B remaining parallel. Also, the rigid plates 3A, 3B perform the function of holding constant the raised ribs 2 with regard to the distance between the raised ribs 2 as set during initial attachment over the affected area.

Chang's invention is not intended to control blood flow as are the raised ribs 2 of the auricular hematoma clamp 1.

The raised rib 2 on the plate 3A of the auricular hematoma clamp 1 is used in conjunction with the opposing raised rib 2 on the opposing plate 3B to enable the process to control the blood flow to and from the area being treated and is not intended to apply pressure to a specific acupressure point, but rather to apply pressure in a linear fashion to the specific area between the two raised ribs 2.

FIG. 2B exhibits an alternate embodiment of a plate 3C of an auricular hematoma clamp 1 of the present invention having a raised rib 2 positioned in different locations along the surface of the plate 3C.

The auricular hematoma clamp 1 is a device used as an alternate for surgery to an affected ear with a hematoma. The raised rib 2 might act as an improvement to Barnes' device for assistance in healing surgery performed for ear alteration. Although the perforations in Barnes' device for adjustment to ear size are an important feature, a better fit is accomplished by trimming the auricular hematoma clamp 1 to fit slightly larger than ear being treated. Pendent ears require flat plates and a rigid material for the said plates 3A, 3B construction.

The raised rib 2 performs the function of maintaining a constant distance between the two said ribs 2 to apply slight pressure to the ear flap thus controlling the amount of blood flow to and from the area affected. The pressure applied need not be enough to stop the flow of blood as per a tourniquet, but only to apply light pressure to inhibit the flow of blood. As the process of healing continues with the auricular hematoma clamp 1 in place, the swelling will decrease, thus decreasing the pressure applied at said raised ribs, allowing for more normal flow of blood to and from the affected area, and for natural healing to take place.

Figure 5:
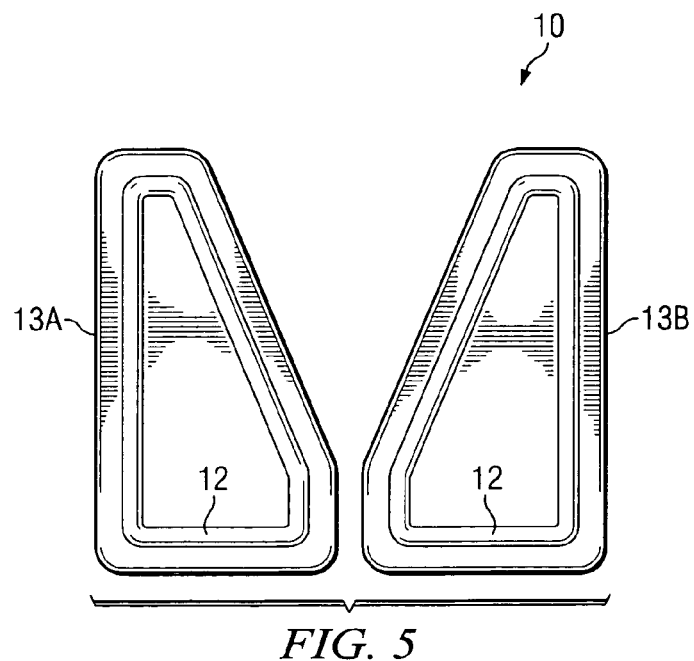
FIG. 5 exhibits an inward plate surface with an area encompassed by the raised rib.

FIG. 5 exhibits an inward plate surface of plates 13A, 13B of an auricular hematoma clamp 10 having a raised rib 12 configured to surround an enclosed area of the inward surface of the plates 13A, 13B.

Figure 6:
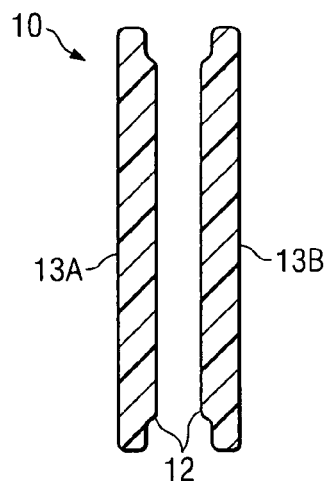
FIG. 6 exhibits a cross-section of FIG. 5.

FIG. 6 exhibits a cross section of the plates 13A, 13B of FIG. 5.

Figure 7:
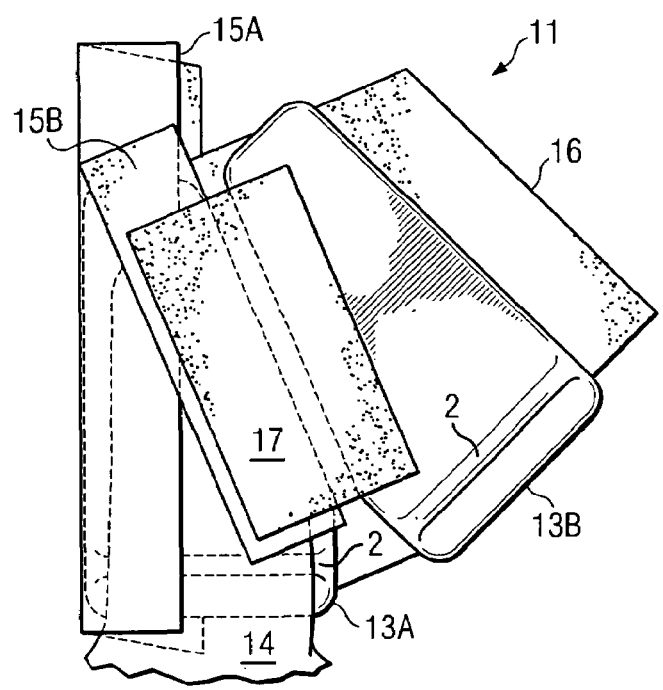
FIG. 7 exhibits an auricular hematoma clamp comprised of two plates, each plate with a raised rib located on the inward surface, whereas one plate is shown properly positioned and secured with athletic tape to a tab and an affected ear, and the second plate is shown attached with athletic tape over the ear and to the other plate.

FIG. 7 exhibits an auricular hematoma clamp 11 comprised of two plates 13A, 13B, each plate 13A, 13B with a raised rib located on the inward surface, whereas one plate 13A is shown properly positioned and secured with athletic tape 15A, 15B to a tab 18 (See FIG. 8) and an affected ear 14, and the second plate 13B is shown ready for attachment with athletic tape 16, 17 over the ear 14 and to the other plate 13A.

Figure 8:
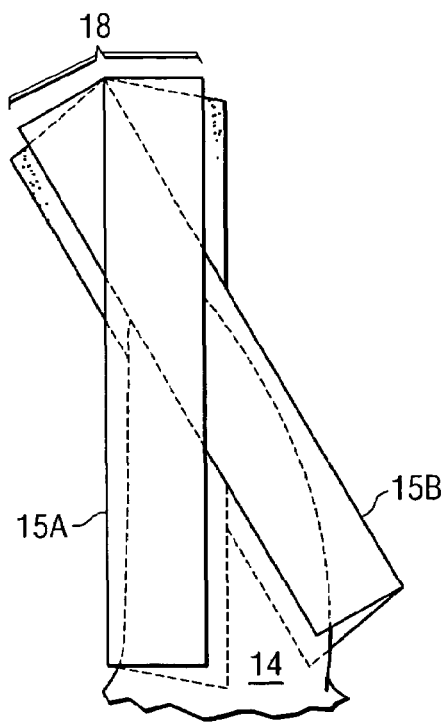
FIG. 8 exhibits the ear prepared with athletic tape folded over the ear's edges forming a tab when the tape is extended beyond the ear.

FIG. 8 exhibits the ear 14 prepared with athletic tape 15A, 15B folded over the ear's 14 edges forming a tab 18 when the tape 15A, 15B is extended beyond the ear 14.

In an alternative embodiment a raised rib 2, as illustrated in FIG. 2B, may be attached to a desired location on said plates, offering variability in treatment without deviating from the original purpose.

Further, a larger surface area of the raised rib at the point of pressure may offer increased restriction of blood flow to and from the affected area.

Another alternative embodiment, preparing the ear with a base application of tape allows the auricular hematoma clamp to have a positive attachment to the ear.

Moreover, the tab 5C of FIG. 4 and the tab 18 of FIG. 8, formed when extending the tape beyond the ear tip, gives the surface area beyond the ear surface to provide for attaching the clamp to the head of the animal.

Finally, the intended function of the auricular hematoma clamp 1 will not be compromised while worn in the pendent position. In other words, the device 1 may be secured by tape disposed over the head of the animal, thereby taking advantage of the small force of gravity imparted upon the ears 4, 14 to allow the ears 4, 14 to be in the pendent position.

In addition to the aforementioned examples, it is made clear that any deviation by those skilled in the art, in materials, attachment procedures, locations of one or all of the features associated are not to be construed as limiting the invention set forth in the appended claims that are to be interpreted as encompassing the spirit and scope of the invention.

What is claimed is:

1. An auricular hematoma clamp for treatment of a hematoma condition in a pendent ear of an animal patient, comprising:
   first and second opposing plates,
   each of said plate to have an inward surface and an outward surface,
   each of said inward surfaces contains a raised rib in an aligned position to oppose said raised rib on the opposing said plate,
   each of said plates to be rigid,
   each of said plates to be lightweight,
   each of said plates to be generally triangular in shape and configured to have a size slightly larger than the pinna of the pendent ear of the animal patient;
   means to secure the plates to the pendent ear; and
   means to secure the plates to the head of the animal patient.

2. The auricular hematoma clamp of claim 1, wherein a raised rib is located near the bottom on the inward surface area of said first and second plates.

3. The auricular hematoma clamp of claim 1, wherein more than one raised rib is located on the inward surface areas of said first and second plates.

4. The auricular hematoma clamp of claim 1, wherein the raised rib is molded in a fashion to encompass an area located on the inward surface area of said first and second plates.

5. The auricular hematoma clamp of claim 1, wherein said plates are of a material to be formed over the contours of the head of the animal patient and still remain rigid.

6. The auricular hematoma clamp of claim 1, wherein the surface areas of the first and second plates are flat.

7. The auricular hematoma clamp of claim 1, wherein the surface areas of the first and second plates are curved.

8. The auricular hematoma clamp of claim 1, wherein the means to secure the plate to the pendent ear is a tape selected from the group consisting of athletic tape and adhesive tape.

9. The auricular hematoma clamp of claim 1, wherein the means to secure the plate to the head of the animal patient is a tape selected from the group consisting of athletic tape and adhesive tape.

10. The auricular hematoma clamp of claim 9, wherein the clamp is disposed in a pendent position with respect to the head of the animal patient to perform the treatment without securing the clamp to the head of the animal patient.

11. The auricular hematoma clamp of claim 1, wherein the outward surfaces are smooth.

12. The auricular hematoma clamp of claim 1, wherein the outward surfaces include features for added rigidity.

13. The auricular hematoma clamp of claim 1, wherein the first and second plates have a size and shape to encompass a portion of the pendent ear corresponding to the area of treatment of the hematoma condition.

14. The auricular hematoma clamp of claim 13, wherein more than one raised rib is disposed at more than one location on the inward surfaces of the first and second plates.

15. The auricular hematoma clamp of claim 1, wherein the raised rib is separate and attachable to said first and second plates.

16. The auricular hematoma clamp of claim 1, wherein the area of a raised rib is increased to perform a larger area of pressure.

17. The auricular hematoma clamp of claim 1, wherein the first and second plates include a piece of adhesive tape for folding over the edges of the animal patient's ear to provide a base for attachment of the first and second plates.

18. The auricular hematoma clamp of claim 17, wherein a tab is formed in the adhesive tape such that it is extendable beyond the tip of the pendent ear of the animal patient.

19. A method of attaching an auricular hematoma clamp wherein the auricular hematoma clamp includes first and second opposing auricular-shaped plates each having at least one raised rib disposed on an inward surface thereof along and proximate a defined edge of each respective plate, and taping means for securing the first and second plates in a clamping manner on respective first and second sides of an auricle, comprising the steps of:
   preparing the ear to be treated, having a hematoma at a hematoma location within the auricle, to receive the first and second plates of the auricular hematoma clamp;
   securing the first plate against the first side of the auricle, the raised rib of the first plate in contact therewith, using a first adhesive tape folded over respective, proximate edges of the plate and auricle;
   positioning the second plate against the second side of the auricle such that the respective raised ribs of the first and second plates are opposingly aligned; and
   clamping with slight pressure the second plate against the second side of the auricle, the raised rib in contact therewith, securing the combination of the auricle disposed between the first and second plates using a second adhesive tape.

20. The method of claim 19, further comprising the step of:
   supporting the clamped auricle in an upward-extending orientation.

21. The method of claim 19, wherein the step of preparing further comprises the steps of:
   aspirating blood pooled at the hematoma location in the auricle of the ear; and
   preparing the ear with adhesive tape strips folded over at least first and second opposite edges of the auricle, to receive the first and second plates.

22. The method of claim 21, wherein the step of preparing further comprises the step of:
   extending excess proximate ends of the folded adhesive tape strips to form tabs for attaching supports to hold the clamped auricle in an upward extending orientation.

23. The method of claim 19, wherein the step of securing comprises the step of: positioning the raise rib across a path between the source of blood entering the auricle and the hematoma location.

24. The method of claim 19, wherein the step of clamping comprises the step of:
adjusting the amount of pressure exerted on the auricle by the clamped first and second plates to limit blood flow into the hematoma location without causing cessation of blood flow thereto.

25. An auricular hematoma clamp for treatment of a hematoma condition in a pendent ear of an animal patient, comprising:
first and second plates having an outline substantially similar to the animal's pendent ear and formed as mirror images, each plate having a rib disposed on an inward surface of the plate substantially along and proximate a defined edge of the plate; and
taping means for securing the first and second plates in a clamping manner on respective first and second sides of the pendent ear of the animal patient to be treated for an auricular hematoma condition, such that the rib on each first and second plate during use will be disposed in juxtaposition against opposite sides of the pendent ear of the animal patient.

26. The auricular hematoma clamp of claim 25, wherein the first and second plates are secured one to the other by the taping means and disposed on respective sides of the pendent ear of the animal patient under said treatment such that a weak clamping pressure is exerted against the opposite sides of the pendent ear by the respective rib on the first and second plates.

27. The auricular hematoma clamp of claim 26, further comprising:
means for adjusting the weak clamping pressure to limit blood flow into a location having the hematoma condition without causing cessation of blood flow thereto.

28. The method of claim 25, wherein the ridge comprises a narrow, elongated hump having a rounded cross-section.

29. The auricular hematoma clamp of claim 25, wherein the defined edge is the portion of the first or second plate for positioning proximate the animal patient's head.

30. The auricular hematoma clamp of claim 25, wherein the taping means comprises flexible adhesive-backed strips for securing two or more items together.

31. The auricular hematoma clamp of claim 25, wherein the first and second plates are configured for trimming the outline of the plates to correspond to the shape of a particular auricle or hematoma condition of an animal patient undergoing said treatment.

* * * * *